(12) United States Patent
Kania et al.

(10) Patent No.: US 10,676,538 B2
(45) Date of Patent: Jun. 9, 2020

(54) **INHIBITORS OF *STAPHYLOCOCCUS PSEUDINTERMEDIUS* SORTASE**

(71) Applicants: Stephen Anthony Kania, Powell, TN (US); David Allen Bemis, Maryville, TN (US); Jerome Baudry, Madison, AL (US); Manasi Balachandran, Knoxville, TN (US)

(72) Inventors: Stephen Anthony Kania, Powell, TN (US); David Allen Bemis, Maryville, TN (US); Jerome Baudry, Madison, AL (US); Manasi Balachandran, Knoxville, TN (US)

( * ) Notice: Subject to any disclaimer, the term of this patent is extended or adjusted under 35 U.S.C. 154(b) by 0 days.

(21) Appl. No.: 16/114,582

(22) Filed: Aug. 28, 2018

(65) Prior Publication Data

US 2019/0241675 A1    Aug. 8, 2019

Related U.S. Application Data

(60) Provisional application No. 62/550,996, filed on Aug. 28, 2017.

(51) Int. Cl.
| | | |
|---|---|---|
| *A61K 38/00* | (2006.01) | |
| *C07K 14/315* | (2006.01) | |
| *A61K 35/74* | (2015.01) | |
| *C07K 16/40* | (2006.01) | |
| *C12N 9/52* | (2006.01) | |
| *A61K 31/519* | (2006.01) | |
| *A61K 31/5375* | (2006.01) | |
| *A61K 31/426* | (2006.01) | |
| *A61K 31/655* | (2006.01) | |

(52) U.S. Cl.
CPC ............ *C07K 16/40* (2013.01); *A61K 31/426* (2013.01); *A61K 31/519* (2013.01); *A61K 31/5375* (2013.01); *A61K 31/655* (2013.01); *C12N 9/52* (2013.01); *C12Y 304/2207* (2013.01)

(58) Field of Classification Search
CPC ....... A61K 38/00; A61K 35/74; C07K 14/315
See application file for complete search history.

(56) References Cited

U.S. PATENT DOCUMENTS

2012/0149710 A1* 6/2012 Jung .................... C07D 231/18
                                                              514/252.02

OTHER PUBLICATIONS

Balachandran, Characterization of Protein A and Sortase A in *Staphylococcus pseudintermedius*: Potential Targets for Novel Therapeutic Approaches; Doctoral Dissertation; May 2017 (Year: 2017).*

* cited by examiner

*Primary Examiner* — Gary B Nickol
*Assistant Examiner* — Lakia J Jackson-Tongue

(57) ABSTRACT

Compounds inhibitory to *Staphylococcus pseudintermedius* Sortase A (SrtA) are identified. The compounds inhibit cell wall-associated protein anchoring to the bacterial cell wall, thus potentially reducing bacterial virulence.

4 Claims, 5 Drawing Sheets

Specification includes a Sequence Listing.

SEQUENCE LISTING

<160> NUMBER OF SEQ ID NOS: 2

<210> SEQ ID NO 1
<211> LENGTH: 597
<212> TYPE: DNA
<213> ORGANISM: Staphylococcus pseudintermedius

<400> SEQUENCE: 1

```
atgcaaaaat taacacgtgg gttggttcca cttattggta ttgcattgat tttagcaggc    60
gtatatttaa tctttaagcc gaaaattgat gcatatttga ccaataaaga aaatgaacaa   120
aaaattgaag tatatgaaga agtcaacaa aatgcaccat caaagtgcc tgaaattccg    180
aaagacccgt cgaaagtcgt tggtgtatta gaagtgccgt cagtcggtat aaaagaagct   240
gtgtatcctg gtcctgcgac acctgaacaa ttggagcgcg gtgtcagttt ggcggaaaag   300
gatgaatcac tcaaagacca aaatatcgct attgcgggac atacgaatta tagtttgaac   360
tatcaattta cagagttaca caaagcgaaa aagggtgcag aagtaatttt taaactgggt   420
aaagaaacgc gcaaatatca aattacgtcg attaaagatg tcgatccgta tcaagttgaa   480
gtgttggaag agatgaagaa agataaagac caactgacac tcattacttg tgatgattac   540
gatgagaaaa caggtcagtg gctgacacgc aaaatttatg tagctgaacg tgtgtag      597
```

<210> SEQ ID NO 2
<211> LENGTH: 198
<212> TYPE: PRT
<213> ORGANISM: Staphylococcus pseudintermedius

<400> SEQUENCE: 2

Met Gln Lys Leu Thr Arg Gly Leu Val Pro Leu Ile Gly Ile Ala Leu
1               5                   10                  15

Ile Leu Ala Gly Val Tyr Leu Ile Phe Lys Pro Lys Ile Asp Ala Tyr
            20                  25                  30

Leu Thr Asn Lys Glu Asn Glu Gln Lys Ile Glu Val Tyr Glu Glu Ser
        35                  40                  45

Gln Gln Asn Ala Pro Ser Lys Val Pro Glu Ile Pro Lys Asp Pro Ser
    50                  55                  60

Lys Val Val Gly Val Leu Glu Val Pro Ser Val Gly Ile Lys Glu Ala

-continued

```
            65                  70                  75                  80

Val Tyr Pro Gly Pro Ala Thr Pro Glu Gln Leu Glu Arg Gly Val Ser
            85                  90                  95

Leu Ala Glu Lys Asp Glu Ser Leu Lys Asp Gln Asn Ile Ala Ile Ala
            100                 105                 110

Gly His Thr Asn Tyr Ser Leu Asn Tyr Gln Phe Thr Glu Leu His Lys
            115                 120                 125

Ala Lys Lys Gly Ala Glu Val Ile Phe Lys Leu Gly Lys Glu Thr Arg
            130                 135                 140

Lys Tyr Gln Ile Thr Ser Ile Lys Asp Val Asp Pro Tyr Gln Val Glu
145                 150                 155                 160

Val Leu Glu Glu Met Lys Lys Asp Lys Asp Gln Leu Thr Leu Ile Thr
                    165                 170                 175

Cys Asp Asp Tyr Asp Glu Lys Thr Gly Gln Trp Leu Thr Arg Lys Ile
                180                 185                 190

Tyr Val Ala Glu Arg Val
            195
```

INHIBITORS OF *STAPHYLOCOCCUS PSEUDINTERMEDIUS* SORTASE

This utility patent application claims the benefit of priority in U.S. provisional patent application Ser. No. 62/550,996 filed on Aug. 28, 2017, the entire disclosure of which is incorporated herein by reference.

REFERENCE TO SEQUENCE LISTING SUBMITTED ELECTRONICALLY

A sequence listing electronically submitted with the present application as an ASCII text file named sortaseSequenceListing.txt, created on Aug. 28, 2018 and having a size of 1,000 bytes, is incorporated herein by reference in its entirety.

TECHNICAL FIELD

The present disclosure relates to treatment strategies against *Staphylococcus pseudintermedius*. In particular, the disclosure relates to identified compounds determined to be inhibitory to *S. pseudintermedius* sortase A (SrtA) which have potential to reduce bacterial virulence and so provide a suitable treatment strategy.

BACKGROUND

*Staphylococcus pseudintermedius* is a skin and mucous membrane commensal of dogs and is the Organism most frequently associated with atopic dermatitis and wound infections in dogs. It is also implicated in the pathogenesis of canine pyoderma. In the past, antimicrobial agents have been used to successfully control *S. pseudintermedius* infections. However, in recent years, there has been an increased prevalence of methicillin resistance and multidrug resistance among *S. pseudintermedius* isolates. This has made treatment of infection difficult due to the limited number of antimicrobial agents used in veterinary medicine. Therefore, there is an urgent need (or the development of alternative, treatment strategies to combat *S. pseudintermedius* infections.

Surface proteins in *S. aureus* harboring a C-terminal sorting signal with an LPXTG motif are covalently attached onto the peptidoglycan cell wall by the enzyme sortase A (SrtA) which is encoded by the srtA gene. This 618 bp gene encodes a protein of 206 amino acids with a molecular weight of 23.59 kDa. The enzyme is a cysteine transpeptidase that recognizes the conserved LPXTG motif in surface proteins and specifically cleaves between the threonine (T) and glycine (G) residues. The active site cysteine of SrtA forms an acyl enzyme intermediate that is relieved by the nucleophilic attack of the amino group of the pentaglycine cross bridge in peptidoglycan synthesis precursors. The N-terminus of the enzyme is located in the cytoplasm while the C-terminal enzymatic region is located across the plasma membrane (type II membrane topology). $His^{120}$, $Cys^{184}$ and $Arg^{197}$ form the catalytic triad of the enzyme and are found to be conserved among sortases in *S. aureus*. Surface proteins attached to peptidoglycan precursors are then incorporated into the bacterial cell wall and displayed on the surface.

There are at least 17-21 surface proteins in *S. aureus* that harbor the LPXTG motif. Most of these proteins are involved in virulence and pathogenesis. SrtA is essential for the functional assembly of all surface proteins harboring an LPXTG motif, and therefore plays a crucial role in the pathogenesis of *S. aureus* infections.

*S. aureus* mutants that do not have a functional srtA gene fail to assemble surface proteins on to the peptidoglycan cell wall. Also, they are unable to form abscess lesions in organ tissues or cause lethal bacteremia in mice models of *S. aureus* infections. Therefore, inhibition of SrtA could result in defective display of all the proteins harboring the LPXTG motif and render the organism less virulent. SrtA inhibitors, therefore, may be useful as anti-infective agents particularly for methicillin and multidrug resistant organisms, by disrupting the pathogenesis of bacterial infections. The earliest described inhibitors of SrtA include methane-thiosulfonates such as MESET, (2-sulfonatoethyl) methane-thiosulfonate and p-hydroxymercuribenzoic acid. All these compounds interact with $Cys^{184}$ and render the enzyme inactive. Other natural or chemical compounds have also been examined for their abilities to inhibit SrtA. Although identification of inhibitors for SrtA has been ongoing for several years, it has gained momentum in the last decade due to the advancements in genomics and proteomics.

However, SrtA in *S. pseudintermedius* has not been previously examined. To satisfy this need in the art, the present investigators identified, cloned and expressed the srtA gene of *S. pseudintermedius* in *E. coli*, and used molecular dynamic simulation to generate a model of *S. pseudintermedius* SrtA. After identifying the active site of *S. pseudintermedius* SrtA, scaffold hopping and molecular docking were combined to virtually screen certain drug databases [NCI (National Cancer Institute Open Database) and ZINC (a database of commercially available compounds for virtual screening maintained by the Department of Pharmaceutical Chemistry, University of California San Francisco, Genentech Hall, San Francisco, Calif.)] to identify candidate inhibitors of *S. pseudintermedius* SrtA. The compounds are hereafter referred to by the identifiers assigned in their database. The identified candidates are suitable for inhibition of *S. pseudintermedius* virulence.

BRIEF DESCRIPTION OF THE DRAWINGS

The accompanying drawing figures incorporated herein and forming a part of the specification, illustrate several aspects of the disclosed recombinant attenuated *S. pseudintermedius* SrtA and inhibitors, and together with the description serve to explain certain principles thereof. In the drawings.

DETAILED DESCRIPTION

The Exhibits appended hereto, the citations referred to in this application and in the accompanying Exhibits, and the gene sequences referred to herein and in the accompanying Exhibits form a part of the disclosure and are incorporated herein in their entirety by reference. It will be appreciated that the embodiment shown and described in this patent application is an illustration of one of the modes best suited to carry out the invention. The invention is capable of other different embodiments, and its several details are capable of modification in various, obvious aspects all without departing from the invention. Accordingly, the drawings and descriptions provided herein will be regarded as illustrative in nature and not as restrictive.

The srtA gene from genome sequences determined for several *S. pseudintermedius* isolates representing the major clonal populations in the United States and Europe isolates was identified by a combination of BLAST (using the *S. aureus* srtA gene as reference) and conserved domain search. The isolates are listed in Table 1. It was found that *S. pseudintermedius* contained a srtA gene homologous to the one

TABLE 1

*S. pseudintermedius* strains studied

| Strain | Sequence Type | Resistance |
|---|---|---|
| 06 3228 | ST68 | R |
| 08 1294 | ST68 | R |
| 08 521a | ST68 | R |
| E140 | ST71 | R |
| 08 1661 | ST71 | R |
| NA16 | ST71 | R |
| NA12 | ST64 | R |

TABLE 1-continued

*S. pseudintermedius* strains studied

| Strain | Sequence Type | Resistance |
|---|---|---|
| NA45 | ST118 | R |
| KM 241 | ST73 | S |
| ED99 | ST25 | S | found in *S. aureus* with a 65% sequence homology to the most similar *S. aureus* srtA gene sequence. The srtA gene in *S. pseudintermedius* is 597 bp in length (SEQ ID NO: 1) and codes for a 198 amino acid protein (SEQ ID NO: 2) with a predicted molecular weight of 22.36 kDa. Multiple sequence alignment (MSA) of the srtA gene from various isolates was performed to generate a consensus sequence. This sequence was used to design primers for conventional and quantitative real-time PCR (qPCR) assays. Conventional PCR with *S. pseudintermedius* srtA-specific primers showed that isolates representing the major clonal populations in the United States and Europe (Table 1) contained the srtA gene.

Figure 1:
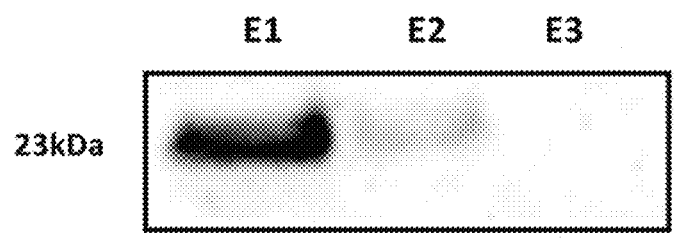
FIG. 1: Western blot analysis was used to characterize *S. pseudintermedius* recombinant SrtA in fractions eluted from a Ni-TED affinity column. His tagged recombinant SrtA was detected with monoclonal anti-His antibody-HRP conjugate (Thermo Scientific. Rockford, Ill.). The molecular weight of the SrtA corresponds to the expected size of approximately 23 kDa. E1, E2 and E3 are three sequential fractions eluted from the Ni-TED affinity column.

A synthetic srtA gene for *S. pseudintermedius* Sortase A with a 6X-His tag at the 3' end was designed, codon optimized for expression in *E. coli*, synthesized and inserted into the expression vector pET11a (GenScript Inc., Piscataway, N.J.). Recombinant colonies were selected on LB agar containing 50 µg/ml ampicillin, picked and inoculated into LB-amp broth and grown overnight at 37° C. One milliliter of overnight culture was inoculated into 100 ml of LB-amp broth and allowed to grow until an $OD_{600}$=0.4-0.6 was reached. Protein expression was induced by adding 1 mM isopropyl 1-thio-β-d-galactopyranoside (IPTG, Sigma-Aldrich, St. Louis, Mo.) at 30° C. for ~4 hr. Cells were harvested by centrifugation at 10,000×g for 30 min and lysed. The lysate was clarified by centrifugal ion and recombinant protein was enriched on an Ni-TED column (PrepEase His-tagged protein purification kit, Affymetrix Inc, Santa Clara, Calif.). His-tagged SrtA was eluted from the column as per the manufacturer's protocol. The purity of the protein was determined by SDS-PAGE and western blot using monoclonal anti-His antibody-HRP conjugate (Thermo Scientific, Rockford, Ill.). The molecular weight of the purified full-length recombinant, his-tagged SrtA protein was ~23 kDa and was confirmed by SDS-PAGE and western blot (FIG. 1). The concentration of the protein was estimated by Bradford method and found to be 0.5-1 mg/ml per 100 ml batch of *E. coli* culture.

The predicted *S. pseudintermedius* SrtA protein sequence was compared to that of *S. aureus* SrtA using the BLAST algorithm and conserved domain search feature in NCBI. Molecular Dynamic (MD) simulation was performed using the bioinformatics tool MOE (Molecular Operating Environment) to generate a 3-D homology model of *S. pseudintermedius* SrtA. Enzyme coordinates were mapped and the catalytic and active sites including the amino acids involved in substrate binding were predicted. The enzyme structure at one of many coordinates was fixed and this structure was initially used to screen the drug database NCI (National Cancer Institute).

Compounds predicted to bind to the active site were identified. Initially, from the 200 highest ranked compounds, twenty were selected. Of the 20, the 10 most active compounds were purchased and tested in the in vitro (FRET) assay. The assay to determine the functional activity of recombinant SrtA and its inhibition was performed in 96-well black microtiter plates with clear bottom (Corning, Fisher Scientific, Hampton, N.H.) in a final reaction volume of 200 µl. Fluorescent-quenched bacterial sortase substrate III, Abz/DNP (Abz-LPETG-K(Dnp)-NH2 (GenScript Inc., Piscataway, N.J.) dissolved in isopropanol was used for Km determination. Varying concentrations of the substrate (2.5 µM-200 µM) were incubated at 25° C. with 1 µM of SrtA diluted in assay buffer (50 mM Tris-HCl, 150 mM NaCl, 5 mM CaCl2, and 0.1% Triton X-100, pH 7.5). The increase in fluorescence was measured in a kinetic assay for 20 min at 2 min intervals using a Synergy HTX multimode reader (BioTek, Winooski, Vt.) at wavelengths 320 excitation/420 emission. The initial velocity V0 was determined from the linear portion of the curve and the Km was determined using the Michaelis-Menten equation where V=Vmax[S]/([S]+Km). To measure the effect of inhibitors recombinant SrtA was pre-incubated with varying amounts of the inhibitor at 37HTX multimod and subjected to the same FRET assay.

Figure 2:
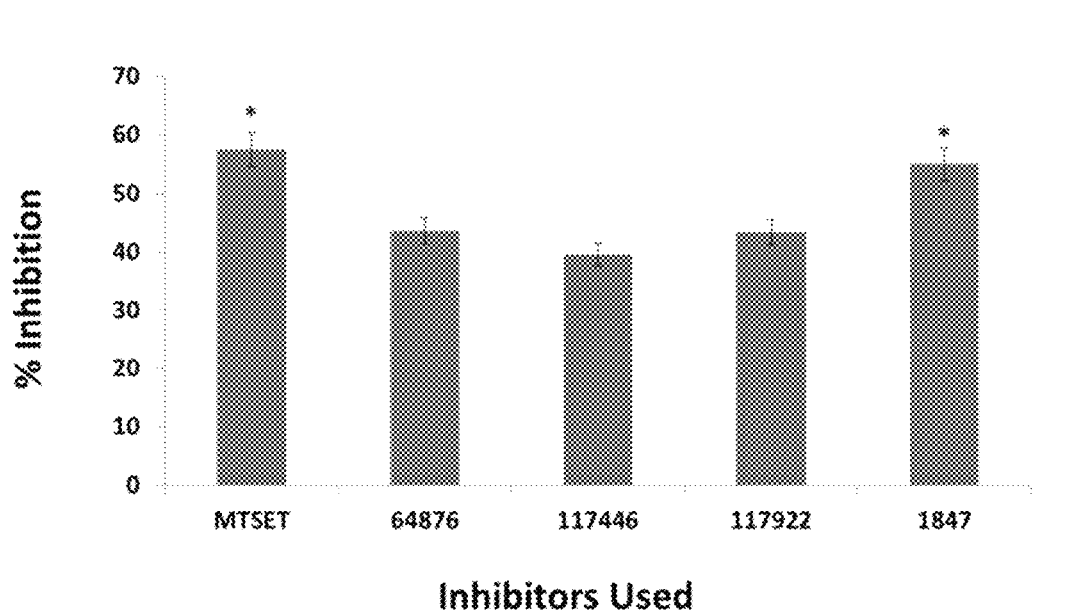
FIG. 2: Compounds from NCI were tested for their ability to inhibit *S. pseudintermedius* recombinant SrtA using the in vitro FRET-based functional assay. The four NCI compounds shown had approximately 40%-60% inhibition of SrtA activity compared to buffer controls. The values represent averages from three independent experiments with the standard deviations shown at the top of each bar. MTSET, a known inhibitor of sortase and NCI inhibitor 1847 differed significantly in their ability to inhibit sortase compared to NCI inhibitors 64876, 117446 and 117922 at *$P<0.05$.

From the first round of screening, four out of the ten compounds from NCI (117466, 117922, 64876 and 1847; see also FIG. 2) showed between 40-60% inhibition of SrtA. Of these, Compound 1847 consistently showed 50-80% inhibition of recombinant SrtA. MTSET which is a known inhibitor of SrtA but which exhibits skin and eye irritation and organ toxicity, was used as the control and showed 57.5% inhibition in this assay.

TABLE 2

Compound Characteristics

| Compound NCI/ZINC | CAS | Molecular Formula |
|---|---|---|
| NCI 1847 | CAS 2484-88-0 | $C_{12}H_{10}N_2O_3S$ |
| NCI 64876 | CAS: 6958-72-1 | $C_{25}H_{32}Cl_2N_2O_4$ |
| NCI 117922 | none | $C_7H_6N_4O_4$ |
| NCI 117446 | 59712-82-2 | $C_{11}H_{19}NO_4S$ |
| ZINC 05930504 | none | $C_{14}H_{11}ClN_4O_2$ |

Figure 3:
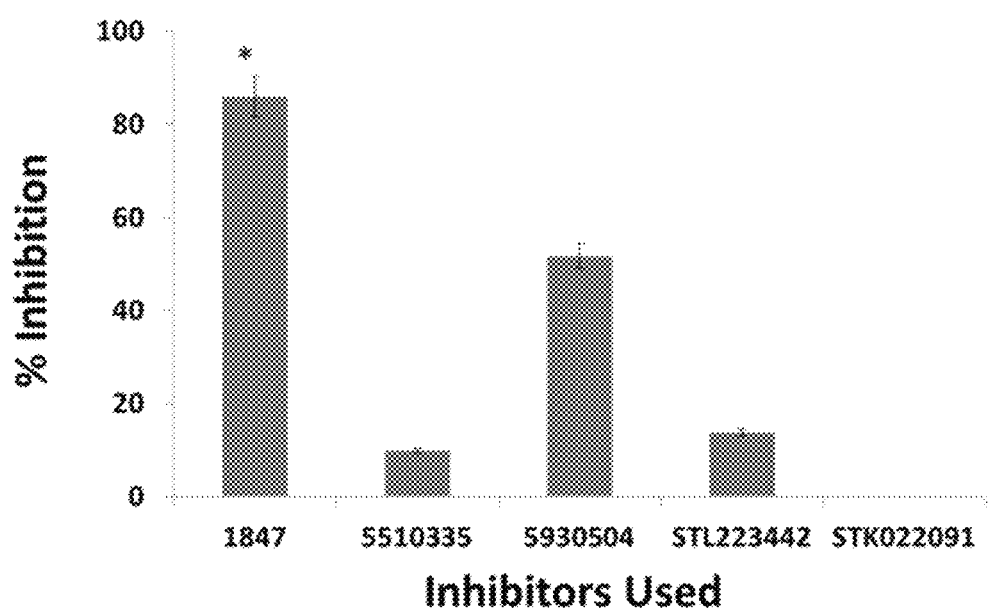
FIG. 3: Compounds identified as candidate inhibitors form the ZINC database were tested for their ability to inhibit *S. pseudintermedius* recombinant SrtA using the in vitro FRET-based functional assay. Of the four ZINC compounds tested, only 5930504 showed approximately 50% inhibition of SrtA in the in-vitro FRET-based functional assay. ZINC compounds 5510335 and STL223422 showed 10-20% inhibition while STK022091 did not have any detectable inhibitory effect on SrtA. The values represent average from three independent experiments and significant difference of 1847 compared to the other compounds was determined at *P<0.05.

Due to the promising results of NCI database compound 1847, a second search iteration was performed based on the structure of 1847 to identify similar compounds possibly having higher inhibitory potential. Four compounds were identified from the ZINC database. Of the four compounds, only one compound, 5930504 (see FIG. 3), showed 51.76% inhibition. 5510335 and STL223442 showed 9.88% and 13.75% inhibition respectively. SKT022091 did not have inhibitory effect on SrtA. However, none of the compounds from ZINC were belter than the parent compound, 1847.

Figure 4:
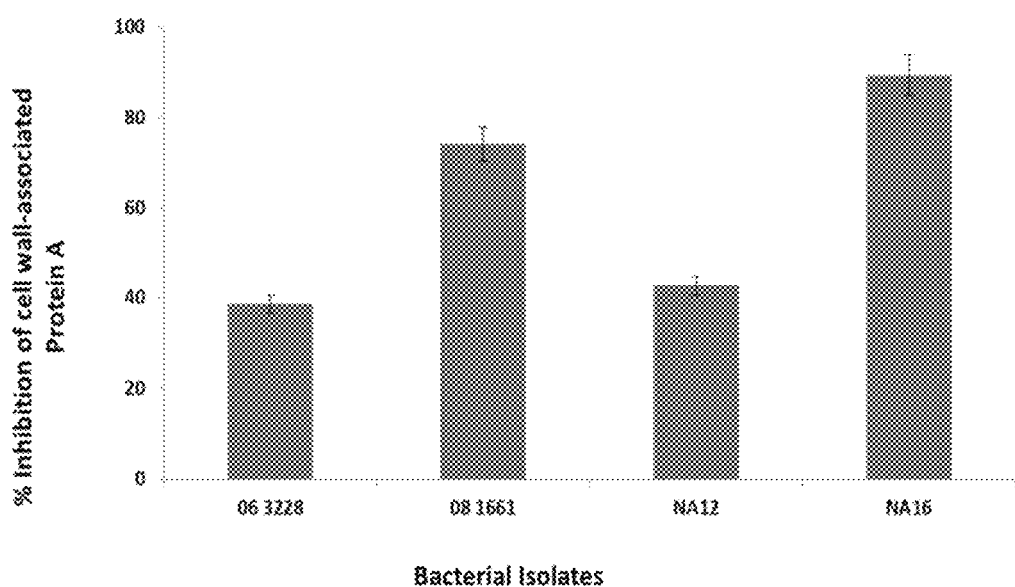
FIG. 4: Four bacterial isolates 08-3228, 08-1661, NA12, NA16 and NA45 were grown in the presence of inhibitor 1847 until exponential log phase. *S. pseudintermedius* recombinant SrtA inhibition was measured indirectly by determining the density of cell wall associated Protein A (one of the LPXTG proteins targeted by SrtA) using flow cytometry. Protein A was detected with FITC conjugated chicken anti-protein A (Gallus immunotech, Cary, N.C.). The values represent average from three independent experiments with the standard deviations shown at the top of each bar.

Inhibition of SrtA in bacterial cells was measured indirectly by measuring the decrease in the amount of Protein A on the bacterial surface using flow cytometry. Five representative S. pseudintermedius isolates were tested. Isolates 06-3228, 08-1661, NA12 and NA16 showed 38.7%, 74.3%, 42.8% and 89.4% reduction in the density cell wall-associated Protein A compared to the respective controls without the inhibitor for each isolate, as a result of SrtA inhibition (FIG. 4). Isolate NA45 was not affected by compound 1847. These results suggest that compared to the controls (without inhibitor), the bacterial cells exposed to the inhibitor 1847 showed a decrease in the density of cell wall-associated Protein A due to inhibition of SrtA, which strongly suggests efficacy of the inhibitor in reducing bacterial virulence.

A thermal shift assay was performed to confirm that inhibitor 1847 binds to the active site of Sortase A. Purified recombinant SrtA was diluted to 1 mg/ml and 10 µM of SrtA was incubated with 4 µM of the inhibitor at 37° C. to facilitate binding of the enzyme to the inhibitor. The native enzyme, enzyme-inhibitor complex and appropriate controls were added to the wells of a 48-well plate (total reaction volume 10 µl/well). The reactions contained SYPRO orange (Invitrogen, Carlsbad, Calif.) purchased as a 5,000× stock and used at a 2× final concentration. The following parameters were set to perform the melt curve analysis in a StepOne (ThermoFisher, Waltham, Mass.) real-time PCR instrument (Step and Hold for 1 mm followed by Initial Mold for 2 min at 25 n.rols were added to the wells of a 48 final temperature of 95 followed b min hold). A change in melting temperature from 71.7 a1 Hold for 2 min at 25 n.rols were added to the welution buffer) in native Sortase A to 86.81° C. (Srt A in PBS) and 86.56 (Srt A in Hig-Tag elution buffer) in 1847-stabilized Sortase A occurred, thereby strongly suggesting that the inhibitor 1847 binds to the active site of Sortase A.

Figure 5:
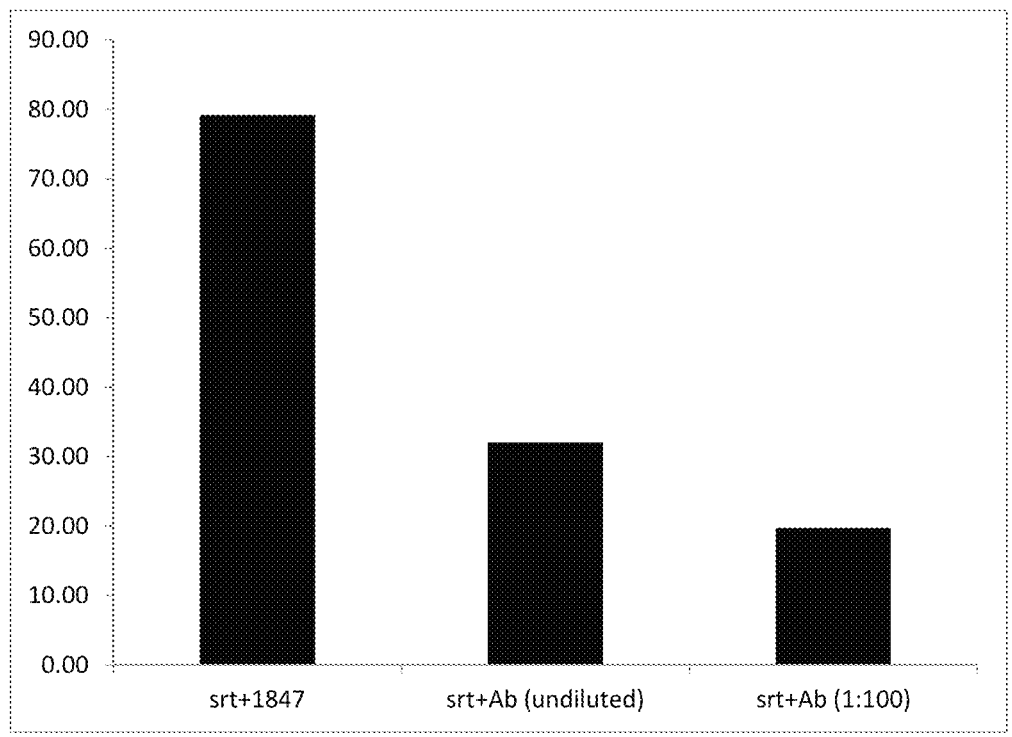
FIG. 5: The inhibitory effect of chicken antibody produced against *S. pseudintermedius* recombinant SrtA was demonstrated in the in-vitro FRET-based functional assay by preincubating the antibody undiluted or diluted 1:100 with SrtA and then measuring the SrtA activity. Percent activity is shown on the vertical axis. The percent inhibition of SrtA activity is shown with 100% activity representing no inhibition. Anti-SrtA inhibited SrtA activity in a concentration dependent manner.

Recombinant SrtA was used to prepare antibodies in chickens reactive with sortase (Aves Labs, Tigards, Oreg.). Two chickens each received four injections of 0.1 mg of SrtA over an 11 week period of time following Aves Labs'b standard protocol. Antibody obtained front the chickens was used to inhibit SrtA activity. The FRET assay was used to measure the inhibitory effect of the antibody and showed a concentration dependent inhibition of sortase activity (FIG. 5).

Summarizing, cell wall-associated (CWA) proteins are responsible for virulence and immune evasion in staphylococci such as S. pseudintermedius. SrtA is a cysteine transpeptidase produced by most Gram positive bacteria which catalyzes the anchoring of proteins harboring the LPXTG motif on to the peptidoglycan cell wall. Inhibition of SrtA may prevent proteins harboring the LPXTG motif from anchoring on to the cell wall, thereby preventing the interaction between the CWA proteins and the host. Since this is a crucial step in the establishment of infection, inhibiting SrtA would reduce bacterial virulence. Advantageously, SrtA is expressed on the outside of the bacterial cell membrane which makes it readily accessible to inhibitors without the need for penetrating the cell membrane. There is no known homologue for SrtA in eukaryotes, thus it is possible to achieve selectivity more easily.

Here, it is shown for the first time that SrtA is present in S. pseudintermedius, and that inhibition thereof by identified candidate molecules reduces CWA protein anchoring to the bacterial cell wall, thus potentially reducing bacterial virulence. In all of the bacterial isolates tested, except NA45, there was between 35%-80% reduction in the amount of CWA Protein A, suggesting strong potential for SrtA inhibition as an anti-infective therapy against staphylococcal infections. Because SrtA and surface proteins with LPXTG sorting signals are present in streptococcal species and other nosocomial pathogens like Enterococcus faecalis, Enterococcus faecium, and Clostridium difficile, inhibitors that can specifically block sortase-catalyzed transpeptidation reaction such as those identified in the present work have potential in treatment strategies against a broad spectrum of pathogenic, antibiotic-resistant Gram-positive bacteria.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the drawings and claims when interpreted in accordance with the breadth to which they are fairly, legally and equitably entitled.

SEQUENCE LISTING

SEQ ID NO: 1: Recombinant SrtA consensus gene sequence
ATGCAAAAATTAACACGTGGGTTGGTTCCACTTATTGGTATTGCATTGAT
TTTAGCAGGCGTATATTTAATCTTTAAGCCGAAAATTGATGCATATTTGA
CCAATAAAGAAAATGAACAAAAAATTGAAGTATATGAAGAAAGTCAACAA
AATGCACCATCAAAGTGCCTGAAATTCCGAAAGACCCGTCGAAAGTCGTT
GGTGTATTAGAAGTGCCGTCAGTCGGTATAAAAGAAGCTGTGTATCCTGG
TCCTGCGACACCTGAACAATTGGAGCGCGGTGTCAGTTTGGCGGAAAAGG
ATGAATCACTCAAAGACCAAAATATCGCTATTGCGGGACATACGAATTAT AGTTTGAACTATCAATTTACAGAGTTACACAAAGCGAAAAAGGGTGCAGA
AGTAATTTTTAAACTGGGTAAAGAAACGCGCAAATATCAAATTACGTCGA
TTAAAGATGTCGATCCGTATCAAGTTGAAGTGTTGGAAGAGATGAAGAAA
GATAAAGACCAACTGACACTCATTACTTGTGATGATTACGATGAGAAAAC
AGGTCAGTGGCTGACACGCAAAATTTATGTAGCTGAACGTGTGTAG SEQ ID NO: 2: Recombinant *S. pseudintermedius* predicted SetA amino acid sequence
MQKLTRGLVPLIGIALILAGVYLIFKPKIDAYLTNKENEQKIEVYEESQQ
NAPSKVPEIPKDPSKVVGVLEVPSVGIKEAVYPGPATPEQLERGVSLAEK
DESLKDQNIAIAGHTNYSLNYQFTELHKAKKKGAEVIFKLGKETRKYQIT
SIKDVDPYQVEVLEEMKKDKDQLTLITCDDYDEKTGQWLTRKIYVAERV

What is claimed is:

1. A method for reducing virulence of a *Staphylococcus pseudintermedius* organism, comprising exposing the organism to at least one inhibitor of *S. pseudintermedius* sortase A.

2. The method of claim 1, wherein the inhibitor is an antibody reactive with *S. pseudintermedius* sortase A.

3. The method of claim 1, including selecting at least one inhibitor from the group of inhibitors consisting of NCI 117446 ($C_{11}H_{19}NO_4S$), NCI 117922 ($C_7H_6N_4O_4$), NCI 64876 ($C_{25}H_{32}Cl_2N_2O_4$), NCI 1847 ($C_{12}H_{10}N_2O_3S$), and ZINC 5930504 ($C_{14}H_{11}ClN_4O_2$).

4. The method of claim 3, wherein the inhibitor is one of NCI 1847 ($C_{12}H_{10}N_2O_3S$) and ZINC 5930504 ($C_{14}H_{11}ClN_4O_2$).

* * * * *